(12) United States Patent
Lappin

(10) Patent No.: US 9,114,017 B2
(45) Date of Patent: Aug. 25, 2015

(54) ROTATABLE REVERSE METAGLENE KIT

(71) Applicant: DePuy Synthes Products, LLC, Raynham, MA (US)

(72) Inventor: Kyle E. Lappin, Fort Wayne, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 14/152,311

(22) Filed: Jan. 10, 2014

(65) Prior Publication Data

US 2014/0128981 A1 May 8, 2014

Related U.S. Application Data

(60) Division of application No. 13/468,171, filed on May 10, 2012, now Pat. No. 8,632,597, and a continuation-in-part of application No. 12/343,272, filed on Dec. 23, 2008.

(51) Int. Cl.
*A61F 2/40* (2006.01)
*A61B 17/86* (2006.01)
*A61F 2/30* (2006.01)

(52) U.S. Cl.
CPC .......... *A61F 2/4081* (2013.01); *A61B 17/86* (2013.01); *A61F 2002/30332* (2013.01); *A61F 2002/30433* (2013.01); *A61F 2002/30507* (2013.01); *A61F 2002/30736* (2013.01); *A61F 2002/30772* (2013.01); *A61F 2002/30878* (2013.01); *A61F 2002/30934* (2013.01); *A61F 2002/4085* (2013.01)

(58) Field of Classification Search
CPC .................................... A61F 2/4081
USPC .......................................... 623/19.11–19.14
See application file for complete search history.

(56) References Cited

U.S. PATENT DOCUMENTS 5,531,793 A 7/1996 Kelman et al.
6,228,119 B1 5/2001 Ondrla et al.
(Continued)

FOREIGN PATENT DOCUMENTS

EP 1323395 7/2003
EP 1591084 11/2005
(Continued)

OTHER PUBLICATIONS

European Patent Office, Search Report in corresponding European patent application (i.e., EP 09 17 8346), dated Apr. 22, 2010 (2 pages).

(Continued)

*Primary Examiner* — Bruce E Snow
*Assistant Examiner* — Brian Dukert
(74) *Attorney, Agent, or Firm* — Maginot, Moore & Beck, LLP

(57) ABSTRACT

A shoulder prosthesis kit includes a first metaglene component including (i) a first body defining an outer diameter, (ii) a first augment extending medially from the first body, and (iii) a first void defined by a portion of the first body and a portion of the first augment, and a plurality of bearing components, each of the plurality of bearing components defining a cavity configured to couple with the first body, and having a bearing surface that is sized differently from the size of another of the plurality of bearing components.

13 Claims, 9 Drawing Sheets

(56) References Cited

U.S. PATENT DOCUMENTS

| | | |
|---|---|---|
| 6,398,812 B1 | 6/2002 | Masini |
| 6,514,287 B2 | 2/2003 | Ondrla et al. |
| 6,699,289 B2 | 3/2004 | Iannotti et al. |
| 6,780,190 B2 | 8/2004 | Maroney |
| 6,821,300 B2 | 11/2004 | Masini |
| 6,863,690 B2 | 3/2005 | Ball et al. |
| 6,953,478 B2 | 10/2005 | Bouttens et al. |
| 7,011,686 B2 | 3/2006 | Ball et al. |
| 7,329,284 B2 | 2/2008 | Maroney et al. |
| 8,241,365 B2 * | 8/2012 | Williams et al. ........... 623/19.11 |
| 8,632,597 B2 | 1/2014 | Lappin |
| 2003/0114933 A1 | 6/2003 | Bouttens et al. |
| 2005/0278030 A1 | 12/2005 | Tornier et al. |
| 2006/0069443 A1 | 3/2006 | Deffenbaugh et al. |
| 2006/0069444 A1 | 3/2006 | Deffenbaugh |
| 2006/0074353 A1 | 4/2006 | Deffenbaugh et al. |
| 2006/0074430 A1 | 4/2006 | Deffenbaugh et al. |
| 2006/0142872 A1 | 6/2006 | Klotz et al. |
| 2007/0142918 A1 * | 6/2007 | Stone ........................ 623/19.13 |
| 2010/0161065 A1 | 6/2010 | Williams, Jr. et al. |
| 2010/0161066 A1 | 6/2010 | Iannotti et al. |
| 2011/0106266 A1 | 5/2011 | Schwyzer et al. |

FOREIGN PATENT DOCUMENTS

| | | |
|---|---|---|
| EP | 2201912 A1 | 6/2010 |
| EP | 2201913 A1 | 6/2010 |
| EP | 2243444 A1 | 10/2010 |
| EP | 2335655 A1 | 6/2011 |
| FR | 2652498 | 4/1991 |
| FR | 2737107 | 1/1997 |
| WO | 2007096741 | 8/2007 |

OTHER PUBLICATIONS

Partial European Search Report corresponding to European Application No. 13166954.1, dated Jul. 25, 2013 (6 pages).

* cited by examiner

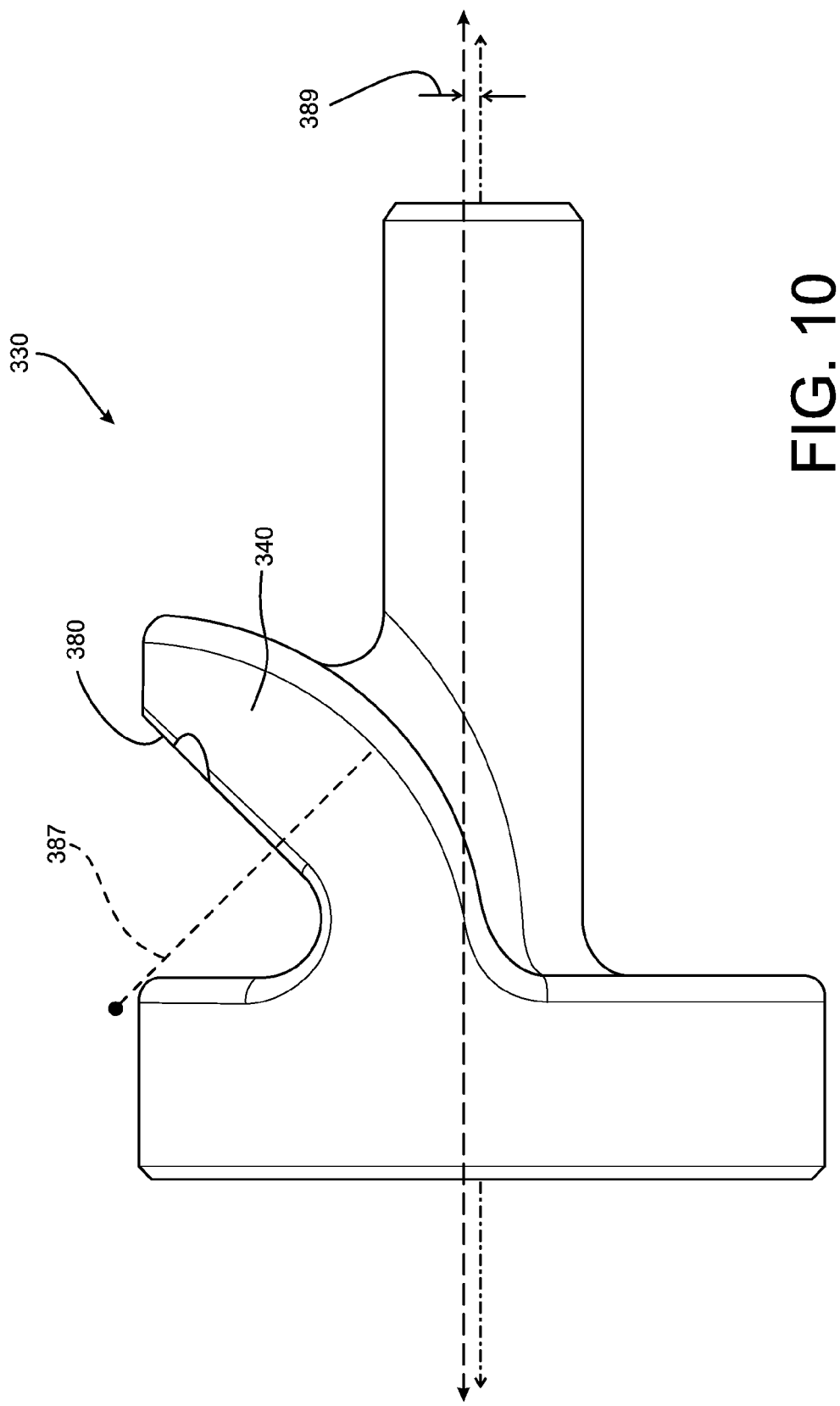

ROTATABLE REVERSE METAGLENE KIT

CROSS-REFERENCE TO RELATED APPLICATIONS

This application is a divisional of U.S. patent application Ser. No. 13/468,171, filed on May 10, 2012, which issued as U.S. Pat. No. 8,632,597 on Jan. 21, 2014, which is a continuation-in-part of U.S. patent application Ser. No. 12/343,272 entitled "Shoulder Prosthesis Having Augmented Metaglene Component for Use in Rotator Cuff Deficient Shoulder", which was filed on Dec. 23, 2008, the entire contents of which are both incorporated herein by reference.

BACKGROUND

The present disclosure relates generally to shoulder prostheses, and more particularly to shoulder prostheses configured for use in rotator cuff deficient shoulders.

The rotator cuff is made up of a group of tendons and muscles which includes the deltoid, the supraspinatus, the infraspinatus, the infrascapular, and the smaller round. When massive rupture occurs of the rotator cuff, only the deltoid muscle remains functional which is insufficient to enable proper operation of the shoulder joint. Moreover, improper operation of the shoulder joint due to massive rotator cuff rupture when left untreated will cause erosion or other defects in the subchondral surface of the glenoid. Thus, it is common that a patient who is being treated for a rotator cuff deficiency will also have erosion or other defects of the subchondral surface of the glenoid.

Certain procedures have been used to treat rotator cuff deficient shoulders which have the above described glenoid erosion or defects. For example, the bone of the glenoid may be asymmetrically prepared to create an appropriately configured support to receive a typical metaglene component of a shoulder prosthesis. Asymmetric preparation of bone involves removing more bone from one side of the glenoid in comparison to another in order to create an even support surface for receipt of the metaglene component. In another example, a bone graft is utilized in conjunction with implantation of a standard metaglene component, the bone graft being configured to fill the eroded or defected area of the glenoid so that the implanted metaglene component is appropriately supported. Yet another example involves interposition shoulder arthroplasty in which new tissue is placed between the damaged surfaces of the joint. In interposition shoulder arthroplasty, a tissue-type graft is sutured over the eroded or defected area of the glenoid so as to ease the pain of the damaged joint while allowing the shoulder joint to retain some function. Interposition shoulder arthroplasty is typically a temporary solution to shoulder joint deficiency, and standard shoulder reconstruction will typically follow after several months.

Each of these treatments has significant drawbacks. For example, implanting a metaglene component in bone that has been asymmetrically prepared results in healthy bone stock being sacrificed. Use of a bone graft in conjunction with a metaglene component may have complications due to graft non-union and not all patients have adequate bone stock available for such a procedure. Interposition shoulder arthroplasty tends to be a short term solution that masks the shoulder joint deficiency, only to be followed some time later by more invasive conventional shoulder reconstruction in which humeral and glenoid components are implanted. This two step process results in more risk and inconvenience to the patient since two surgical procedures are involved.

What is needed therefore is an improved shoulder prosthesis for use in a rotator cuff deficient shoulder that involves glenoid erosion or defects. What is also needed is a shoulder prosthesis for use in a rotator cuff deficient shoulder that involves glenoid erosion or defects that conserves healthy bone stock. What is further needed is a shoulder prosthesis for use in a rotator cuff deficient shoulder that involves glenoid erosion or defects that does not necessitate a bone graft to be implanted in conjunction with the shoulder prosthesis. What is additionally needed is a shoulder prosthesis for use in a rotator cuff deficient shoulder that involves glenoid erosion or defects which does not promote a two stage surgical approach to restoring proper function of the shoulder joint.

SUMMARY

In accordance with one embodiment of the disclosure, there is provided a metaglene assembly for use in a shoulder prosthesis. The metaglene assembly includes a metaglene body, an augment, a void, at least one fastener hole, and at least one fastener. The metaglene body has a lateral, prosthesis-facing side, and a medial, bone-facing side. The augment extends medially from the medial, bone-facing side of the metaglene body. The void is defined by a portion of the medial, bone-facing side of the metaglene body and a lateral portion of the augment. The fastener hole extends from the void through the augment. The fastener is configured to extend within the fastener hole.

Pursuant to another embodiment of the disclosure, there is provided a shoulder prosthesis kit. The shoulder prosthesis includes a plurality of metaglene components and a plurality of bearing components. Each of the metaglene components has a body, an augment extending from the body, and a void defined by a portion of the body and a portion of the augment. At least two of the metaglene components' bodies have outermost diameters that are different from one another. At least two of the bearing components have innermost diameters that are slightly larger than the outermost diameters of respective metaglene components.

In yet another embodiment, a shoulder prosthesis kit includes at least one metaglene component including (i) a metaglene body having a lateral, prosthesis-facing side, and a medial, bone-facing side, the metaglene body defining an outer body perimeter which when projected onto a plane perpendicular to a longitudinal axis of the metaglene body is circularly shaped, (ii) an augment extending medially from the medial, bone-facing side of the metaglene body, the augment defining an outer augment perimeter which when projected onto the plane is semi-circularly shaped, and the projected augment perimeter coincides with at least a portion of the projected metaglene body perimeter, (iii) a void defined by a portion of the medial, bone-facing side of the metaglene body and a lateral facing portion of the augment, and (iv) at least one augment fastener hole extending from the void through the augment, a plurality of bearing components, each of the plurality of bearing components defining a cavity configured to couple with the metaglene body, and having a bearing surface that is sized differently from the size of another of the plurality of bearing components, and at least one fastener configured to be inserted into the at least one augment fastener hole.

In a further embodiment, a metaglene assembly kit for use in a shoulder prosthesis includes a metaglene component including (i) a lateral, prosthesis-facing side, and a medial, bone-facing side, (ii) an augment extending medially from the medial, bone-facing side of the metaglene body, (iii) a void defined by a portion of the medial, bone-facing side of the metaglene body and a lateral facing portion of the augment, (iv) a first fastener hole extending from the void through the augment and defining a first fastener hole axis; and (v) a second fastener hole extending through the metaglene body and defining a second fastener hole axis, the second fastener hole axis aligned with the first fastener hole axis, and a plurality of bearing components, each of the plurality of bearing components defining a cavity configured to couple with the metaglene component, and having a bearing surface that is sized differently from the size of another of the plurality of bearing components.

The above described features and advantages, as well as others, will become more readily apparent to those of ordinary skill in the art by reference to the following detailed description and accompanying drawings. While it would be desirable to provide a metaglene assembly for use in a shoulder prosthesis or a shoulder prosthesis kit that includes one or more of these advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

FIG. 10 is yet another alternative embodiment of a metaglene component configured for use in the metaglene assembly of FIG. 4.

DESCRIPTION OF THE PREFERRED EMBODIMENTS

Figure 1:
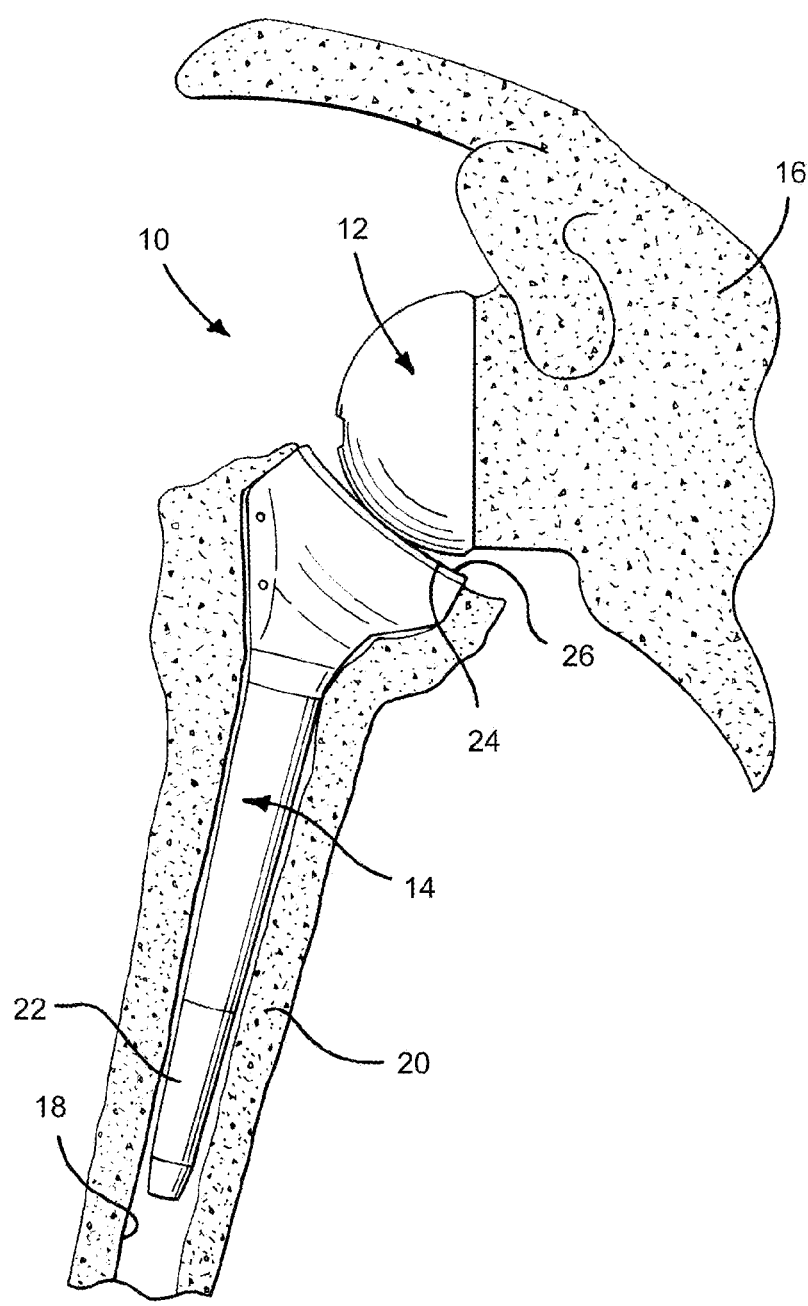
FIG. 1 is a perspective view of a shoulder prosthesis implanted in a scapula and a humerus of a patient to form a joint therebetween.

While the shoulder prosthesis described herein is susceptible to various modifications and alternative forms, specific embodiments thereof have been shown by way of example in the drawings and will herein be described in detail. It should be understood, however, that there is no intent to limit the shoulder prosthesis to the particular forms disclosed, but on the contrary, the intention is to cover all modifications, equivalents, and alternatives falling within the spirit and scope of the invention as defined by the appended claims.

As used herein, the terms "medial" and "lateral" are anatomical directional terms referring to positioning relative to the center of the body receiving the shoulder prosthesis. The term "medial" means closer to the center of the body. The term "lateral" means farther from the center of the body.

Referring to FIG. 1, there is shown a shoulder prosthesis 10 that includes a glenoid component 12 and a humeral component 14 that are configured to cooperate with each other to form a shoulder joint. The glenoid component 12 is configured to be attached to a glenoid of a scapula 16, while the humeral component 14 is configured to be implanted in an intramedullary canal 18 of a humerus 20 as shown in FIG. 1.

The humeral component 14 includes a stem 22 that is configured to be received in the intramedullary canal 18 as shown in FIG. 1. The humeral component 14 further includes a humeral bearing component 24 that has a humeral bearing surface 26.

Figure 2:
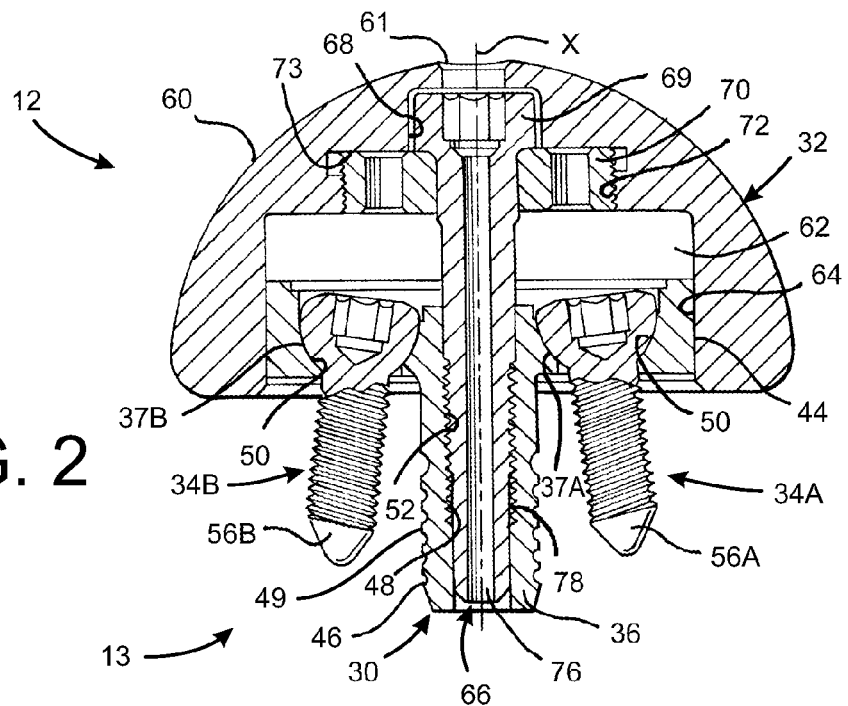
FIG. 2 is a cross sectional view of a glenoid component of the shoulder prosthesis of FIG. 1.
Figure 3:
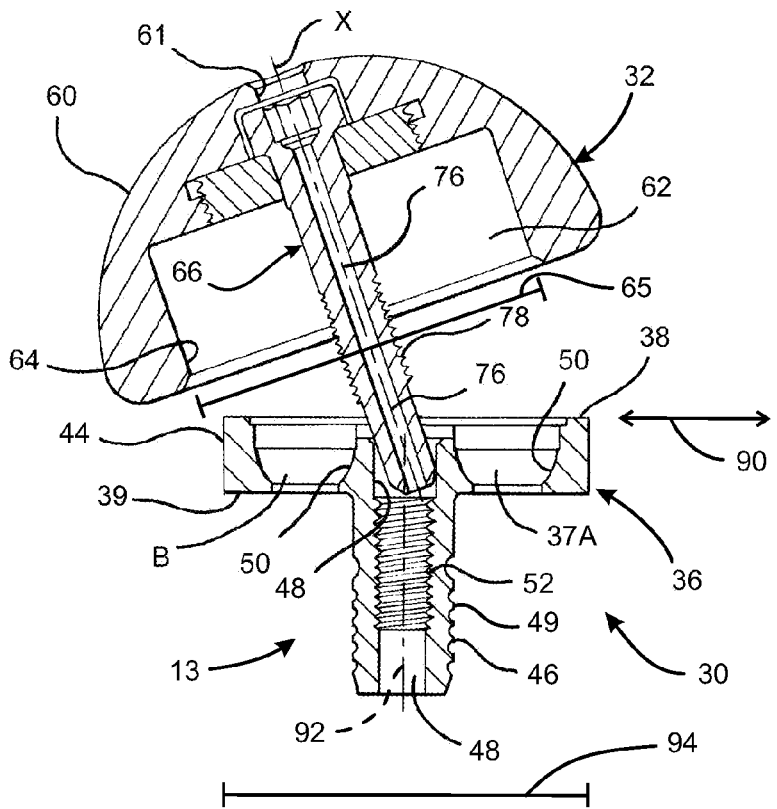
FIG. 3 is an exploded cross sectional view of the glenoid component of FIG. 2, shown with the fasteners removed for clarity of description.

The glenoid component 12 of the shoulder prostheses 10 is shown in more detail in FIGS. 2-3. In particular, as shown in FIG. 2, the glenoid component 12 includes a metaglene assembly 13 and a glenoid bearing component 32. The metaglene assembly 13 includes a metaglene component 30 and a plurality of fasteners 34. The metaglene component 30 is configured to be attached to the glenoid of the scapula 16 (shown in FIG. 1) with the fasteners 34, while the glenoid bearing component 32 is configured to be coupled to the metaglene component 30 as shown in FIGS. 2 and 3.

As shown in FIG. 3, the metaglene component 30 includes a metaglene body 36 having a lateral, prosthesis-facing side 38 and a medial, bone-facing side 39. The lateral, prosthesis-facing side 38 defines a lateral metaglene plane 90. The lateral, prosthesis-facing side 38 of the metaglene body 36 is substantially circularly shaped and defines a metaglene body center (not shown). The metaglene body 36 further has an external peripheral wall surface 44 having an outermost diameter 94 that defines an external coupling surface that extends between the lateral, prosthesis-facing side 38 and the medial, bone-facing side 39. The external peripheral wall surface 44 tapers slightly outwardly from the lateral, prosthesis-facing side 38 to the medial, bone-facing side 39 such that the metaglene body 36 is slightly larger at the medial, bone-facing side 39 than at the lateral, prosthesis-facing side 38. The external peripheral wall surface 44 extends completely (i.e. 360 degrees) around the periphery of the metaglene component 30. The metaglene body 36 has defined therein a plurality of metaglene body fastener holes 37A, 37B, and two other metaglene body fastener holes (not shown). The metaglene body fastener holes 37A, 37B are defined, in part, by walls having concave bearing seats 50.

The metaglene component 30 also includes a post 46 extending from the metaglene body 36. The post 46 defines a post axis 92 that is perpendicular to the lateral metaglene plane 90 and passes through the metaglene body center. The post 46 is attached to the metaglene body 36 by being integrally formed therewith. A plurality of ribs 49 are defined on the post 46. The post 46 has defined therein a central passage 48. The central passage 48 extends through the metaglene body 36 as shown in FIGS. 2-3. The post 46 also includes an internally threaded wall portion 52.

As stated above, the metaglene assembly 13 further includes metaglene body fasteners 34A, 34B, and two other metaglene body fasteners (not shown). Each of the metaglene body fasteners 34A-D includes a head having a convex surface to be matingly received by a respective concave bearing seat 50 of a respective metaglene body fastener hole 37A-D, as shown in FIGS. 2-3, such that the metaglene body fasteners 34A-D do not extend above the concave bearing seats 50. Additionally, each of the metaglene body fasteners 34A-D is configured to be adjustable to any one of a variety of angles with respect to the metaglene body 36 due to the spherical shape of both the fastener heads and the concave bearing seats 50.

Two of the metaglene body fasteners can be locking fasteners wherein advancement of an expander (not shown) into a head recess (not shown) of its respective head causes the fastener head to expand thereby locking the head and thus the metaglene body fastener to the metaglene body 36. Alternatively, more or fewer than two of the metaglene body fasteners can be locking fasteners.

As is shown in FIGS. 2-3, the glenoid bearing component 32 includes a substantially hemispherical glenoid bearing surface 60 that defines an axis "X". The glenoid bearing surface 60 has an access opening 61 defined therein. The glenoid bearing surface 60 is configured to mate with the humeral bearing surface 26 of the humeral bearing component 24 as shown in FIG. 1. In particular, the glenoid bearing surface 60 defines a convex surface and the humeral bearing surface 26 defines a concave surface which is configured to receive the convex glenoid bearing surface 60. Alternatively, the glenoid bearing surface 60 may be configured to define a concave surface and the humeral bearing surface 26 may be configured to define a convex surface which is configured to receive the alternative concave glenoid bearing surface 60.

In addition, the glenoid bearing component 32 defines a cavity 62. The cavity 62 defines an internal wall surface 64 having an innermost diameter 65 that defines an internal coupling surface. The internal wall surface 64 extends completely (i.e. 360 degrees) around the cavity 62. The innermost diameter 65 is sized slightly larger than the outermost diameter 94 of the external peripheral wall surface 44 of the metaglene body 36, and the external peripheral wall surface 44 is positioned in contact with the internal wall surface 64 to form a friction fit connection between the glenoid bearing component 32 and the metaglene component 30 as shown in FIGS. 2-3. In order to facilitate the friction fit connection, both the external peripheral wall surface 44 and the internal wall surface 64 are tapered so that the surfaces 44, 64 when joined together form a Morse taper connection.

Figure 4:
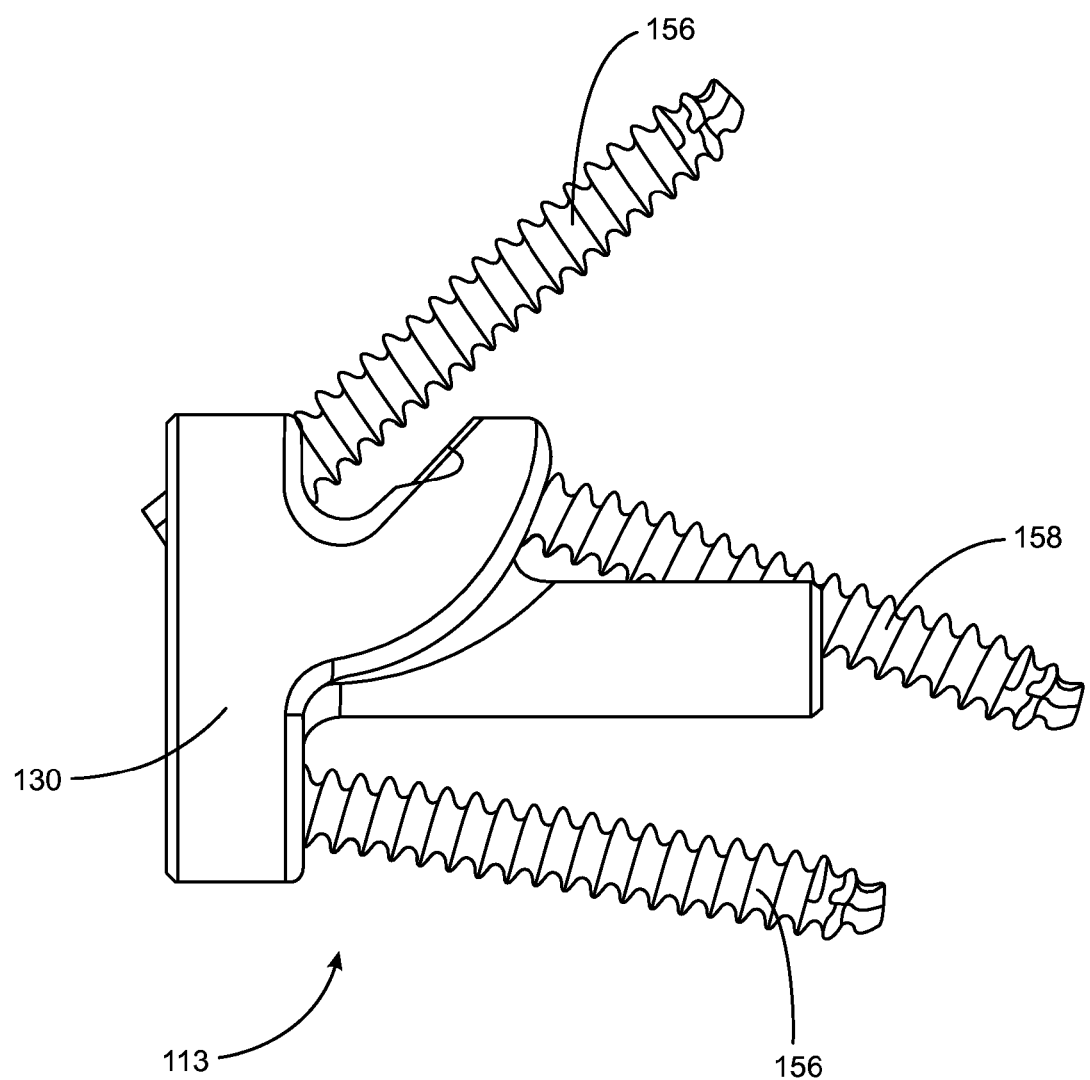
FIG. 4 is a side perspective view of a metaglene assembly of the present disclosure that can be used in the glenoid component of the shoulder prosthesis of FIGS. 1-3.

The glenoid bearing component 32 further includes a screw 66 that is aligned with the axis X. As shown in FIG. 2, the glenoid bearing component 32 further defines a space 68 in which a head 69 of the screw 66 is retained by a washer 70. In particular, the glenoid bearing component 32 further defines an internally threaded wall 72 which meshes with external threads 73 of the washer 70. So retained, the screw 66 is free to rotate in relation to the bearing surface 60. The screw 66 includes a longitudinal axial channel 76 as shown in FIGS. 2-4. The screw 66 also includes an externally threaded portion 78 that is configured to meshingly engage the internally threaded portion 52 of the post as shown in FIGS. 2 and 3. Further structure and operation of the screw and related components may be understood with reference to similar structure disclosed in U.S. Pat. No. 6,953,478 issued to Bouttens et al., the disclosure of which is herein incorporated by reference in its entirety.

Figure 5:
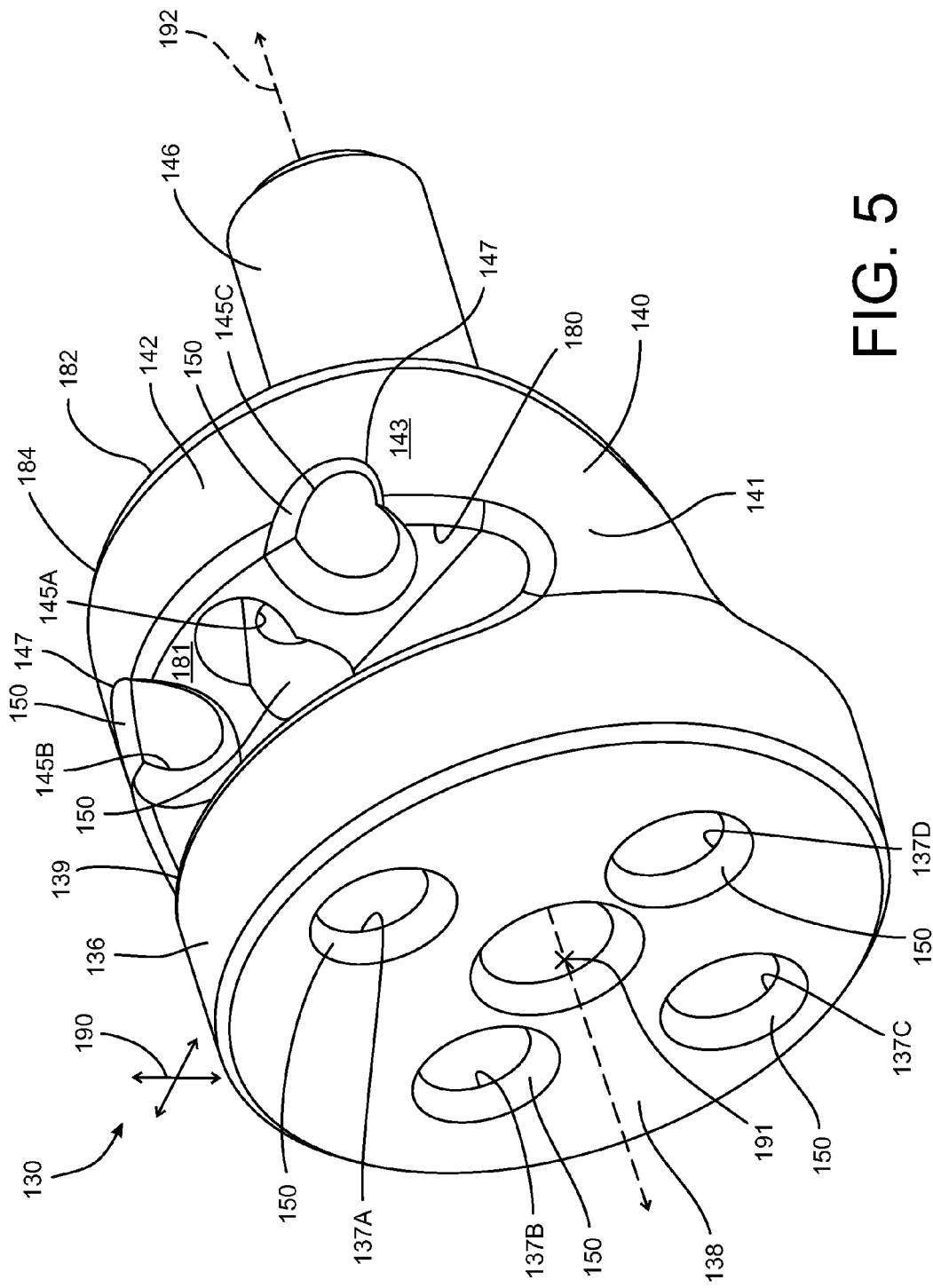
FIG. 5 is a side perspective view of the metaglene component of the metaglene assembly of FIG. 4.

FIG. 4 depicts a metaglene assembly 113 of the present disclosure which can be used in the glenoid component 12 of FIGS. 1-3 in place of the metaglene assembly 13. The metaglene assembly 113 includes a metaglene component 130 and fasteners 156 and 158. FIG. 5 shows the metaglene component 130 in more detail. The metaglene component 130 is configured and used in substantially the same manner as the metaglene component 30 described hereinabove. The metaglene component 130, however, includes additional features described below which provide additional advantages over the metaglene component 30 of FIGS. 1-3.

As shown in FIG. 5, the metaglene component 130 includes a metaglene body 136, a post 146, an augment 140, and a void 180. The metaglene body 136 has a lateral, prosthesis-facing side 138 and a medial, bone-facing side 139. The lateral, prosthesis-facing side 138 of the metaglene body 136 defines a lateral metaglene plane 190 having a metaglene body center 191. The post 146 defines a post axis 192 extending longitudinally through the post 146 perpendicularly to the metaglene plane 190. The metaglene component 130 is arranged substantially radially around the post axis 192. Thus, features of the metaglene component 130 can be referred to as being closer to or farther from the post axis 192 regardless of the orientation of the metaglene component 130.

The augment 140 is attached to the medial, bone-facing side 139 of the metaglene body 136. The augment 140 is attached to the metaglene body 136 by being integrally formed therewith. Alternatively, the augment 140 can be removably attached to the metaglene body 136 by a coupling mechanism (not shown). For example, the coupling mechanism may include a post (not shown) attached to the augment and a recess (not shown) formed in the metaglene body 136, in which the post and recess mate in a friction fit manner to secure the augment 140 to the metaglene body 136.

The augment 140 has a lateral augment surface 181, a medial augment surface 182, a lateral portion 141, and a medial portion 142 and defines an external sidewall 143 that extends between the lateral augment surface 181 and the medial augment surface 182 and extends along both the lateral portion 141 and the medial portion 142. The void 180 is formed between the lateral augment surface 181 of the augment 140 and the medial, bone-facing side 139 of the metaglene body 136. The intersection between the external sidewall 143 and the medial augment surface 182 forms an augment edge 184.

Figure 6:
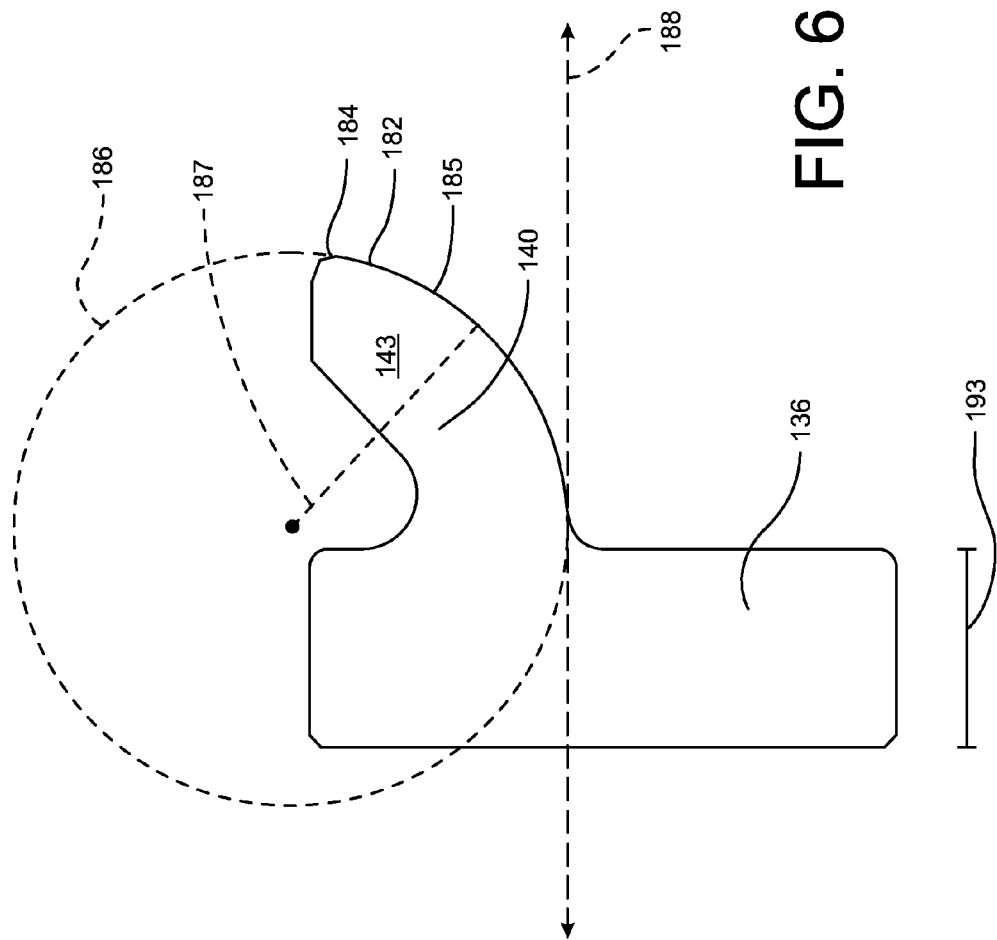
FIG. 6 is a schematic diagram of a side projection of a portion of the metaglene component of FIG. 5.

To clarify the arrangement and configuration of the features of the metaglene component 130, FIG. 6 depicts a projection of a side of the metaglene body 136 and the augment 140 onto a plane. As seen in FIG. 6, when viewed from a side perspective, the augment edge 184 (formed at the intersection of the external sidewall 143 and the medial augment surface 182) forms an augment arc 185 that extends along a portion of an augment circle 186. The augment circle 186 has an augment radius 187 that extends from the augment edge 184 to the center of the augment circle 186. The augment edge 184 departs from the augment circle 186 near the intersection of the augment 140 with the metaglene body 136. A medial augment line 188 indicates where the augment edge 184 departs from the augment circle 186. The medial augment line 188 is parallel to the post axis 192 (shown in FIG. 4). Also shown most clearly in FIG. 6, the metaglene body 136 has a thickness 193.

Figure 7:
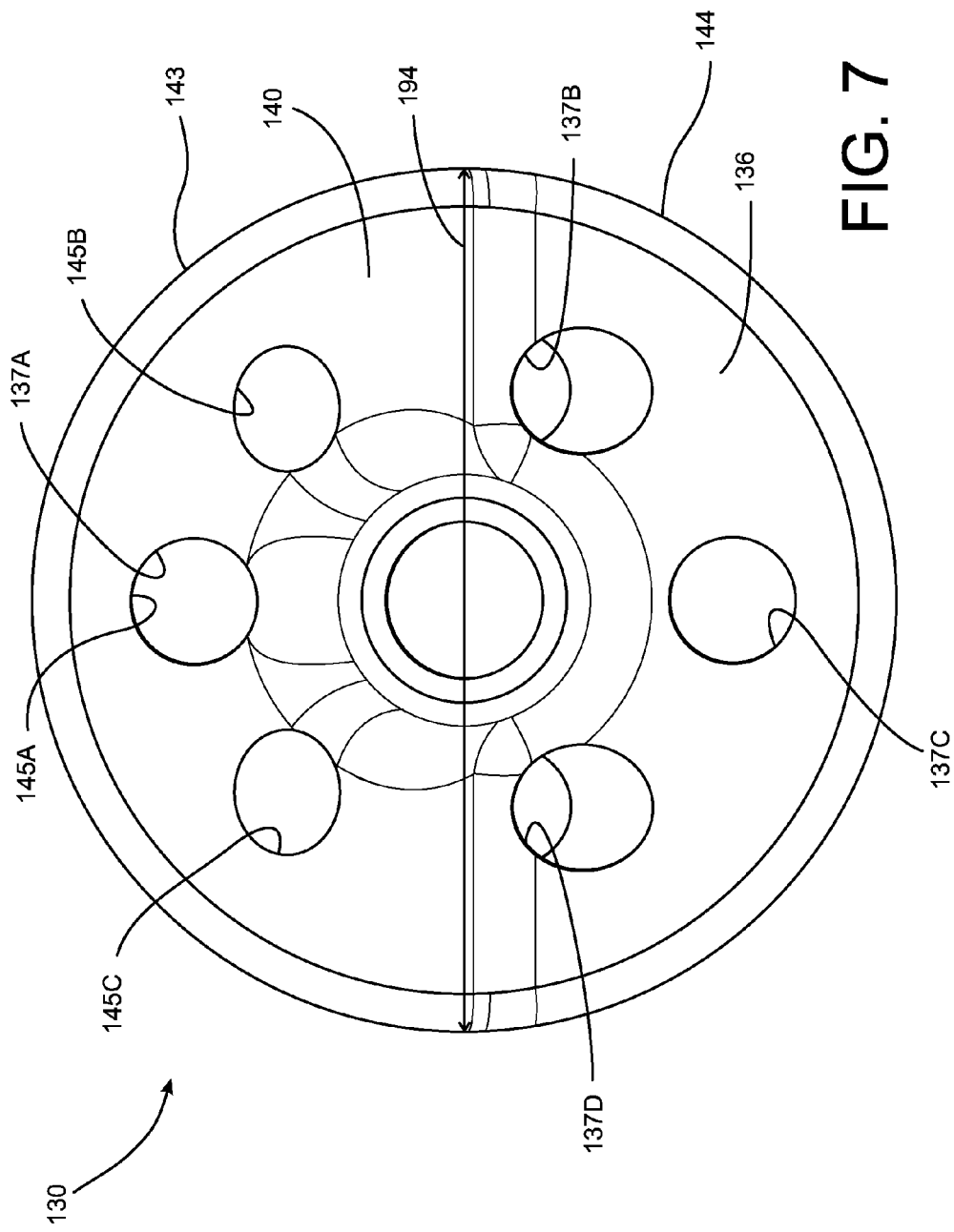
FIG. 7 is a bottom view of the metaglene component of FIG. 5.

FIG. 7 depicts an end view of the metaglene component 130 having an outermost diameter 194. The outermost diameter 194 is sized slightly smaller than the innermost diameter 65 of the glenoid bearing component 32 (shown in FIGS. 2-3) to form a frictional fit in a glenoid component as described above with relation to the glenoid component 12 of FIGS. 1-3. The external sidewall 143 of the augment 140 aligns with a portion of the external peripheral wall surface 144 of the metaglene body 136. In other words, the perimeter of the augment 140 coincides with a portion of the perimeter of the metaglene body 136. In the embodiment of the metaglene component 130 shown in FIG. 7, the external sidewall 143 of the augment 140 extends circumferentially for approximately a half of the extent of the external coupling surface 144 of the metaglene body 136. In other words, the external sidewall 143 of the augment 140 extends circumferentially for approximately 180 degrees around the periphery of the metaglene body 136. In other embodiments, however, the external sidewall of the augment can extend circumferentially for more than or less than a half of the extent of the external coupling surface of the metaglene body.

As shown in FIGS. 5 and 7, the metaglene component 130 has defined therein a plurality of metaglene body fastener holes 137A-D like the metaglene body fastener holes 37A-D described above with reference to the metaglene component 30 (shown in FIGS. 2-3). Additionally, the augment 140 of the metaglene component 130 has defined therein a plurality of augment fastener holes 145A, 145B, and 145C. The augment fastener holes 145A, 145B, and 145C are defined, in part, by walls having concave bearing seats 150 (shown in FIG. 5) like those of the metaglene body fastener holes 137A-D.

As can be seen in FIGS. 5 and 7, the augment fastener hole 145A aligns with the metaglene body fastener hole 137A. As used herein, when holes "align" they are oriented such that a fastener extending through a first hole can also extend through a second hole without changing angle. In contrast, the augment fastener holes 145B and 145C do not align with metaglene body fastener holes. Additionally, the augment fastener holes 145B and 145C extend through the metaglene component 130 at angles different than the angles at which the augment fastener hole 145A and the metaglene body fastener holes 137A, 137B, 137C, and 137D extend through the metaglene component 130. As shown in FIG. 6, the augment fastener holes 145A, 145B, and 145C can be accessed through the void 180. Due to the placement and the angle of the augment fastener holes 145B and 145C, lateral end openings 147 of augment fastener holes 145B and 145C are partially defined in the external side wall 143.

Returning now to FIG. 4, the metaglene assembly 113 further includes metaglene body fasteners 156 and augment fasteners 158. For simplicity, only two metaglene body fasteners 156 and one augment fastener 158 are shown. The metaglene body fasteners 156 can be identical to or different from the augment fasteners 158. The metaglene body fasteners 156 are configured to extend through the metaglene body fastener holes 137A, 137B, 137C, and 137D (shown in FIG. 5), and the augment fasteners 158 are configured to extend through the augment fastener holes 145B and 145C (shown in FIG. 5). The metaglene body fastener 156 that extends through the augment fastener hole 145A (shown in FIG. 5) is configured to additionally extend through metaglene body fastener hole 137A (shown in FIG. 5). However, as shown in FIG. 4, the metaglene body fastener 156 that extends through augment fastener hole 145A (shown in FIG. 5) does not necessarily extend through metaglene body fastener hole 137A (shown in FIG. 5).

Each of the metaglene body fasteners 156 includes a head having a convex surface configured to be matingly received by a respective concave bearing seat 150 of the respective metaglene body fastener hole 137A-D. Each of the metaglene body fasteners 156 is configured to be adjustable to any one of a variety of angles with respect to the metaglene body 136 due to the spherical shape of both the fastener heads and the concave bearing seats 150. Accordingly, depending on the angle at which a metaglene body fastener 156 is inserted through a metaglene body fastener hole 137, the metaglene body fastener 156 does not necessarily extend laterally beyond the plane 190 (shown in FIG. 5). Similarly, each of the augment fasteners 158 includes a head having a convex surface configured to be matingly received by a respective concave bearing seat 150 of the respective augment fastener hole 145A-D. Each of the augment fasteners 158 is configured to be adjustable to any one of a variety of angles with respect to the metaglene body 136 due to the spherical shape of both the fastener heads and the concave bearing seats 150. Accordingly, the augment fastener 158 does not typically extend into the void 180, although a portion of it may extend into the void 180 depending on the angle at which an augment fastener 158 is inserted through an augment fastener hole 145.

When a shoulder prosthesis is implanted into a body, the appropriate metaglene component for use in the metaglene assembly is selected based on the properties of the defect(s) in the bones of the shoulder joint. To most effectively compensate for the defect(s) in the shoulder, the best metaglene component has a metaglene body with the appropriate metaglene body thickness, an augment and metaglene body extending for an appropriate length relative to the post, and an augment extending at an appropriate angle relative to the metaglene body. These factors, among others, influence the particular size and shape of the metaglene component. Because, as noted above, the metaglene component is arranged substantially radially around the post, the metaglene component can be rotated and inserted at any angle appropriate to compensate for the defect(s) in the shoulder.

Figure 8:
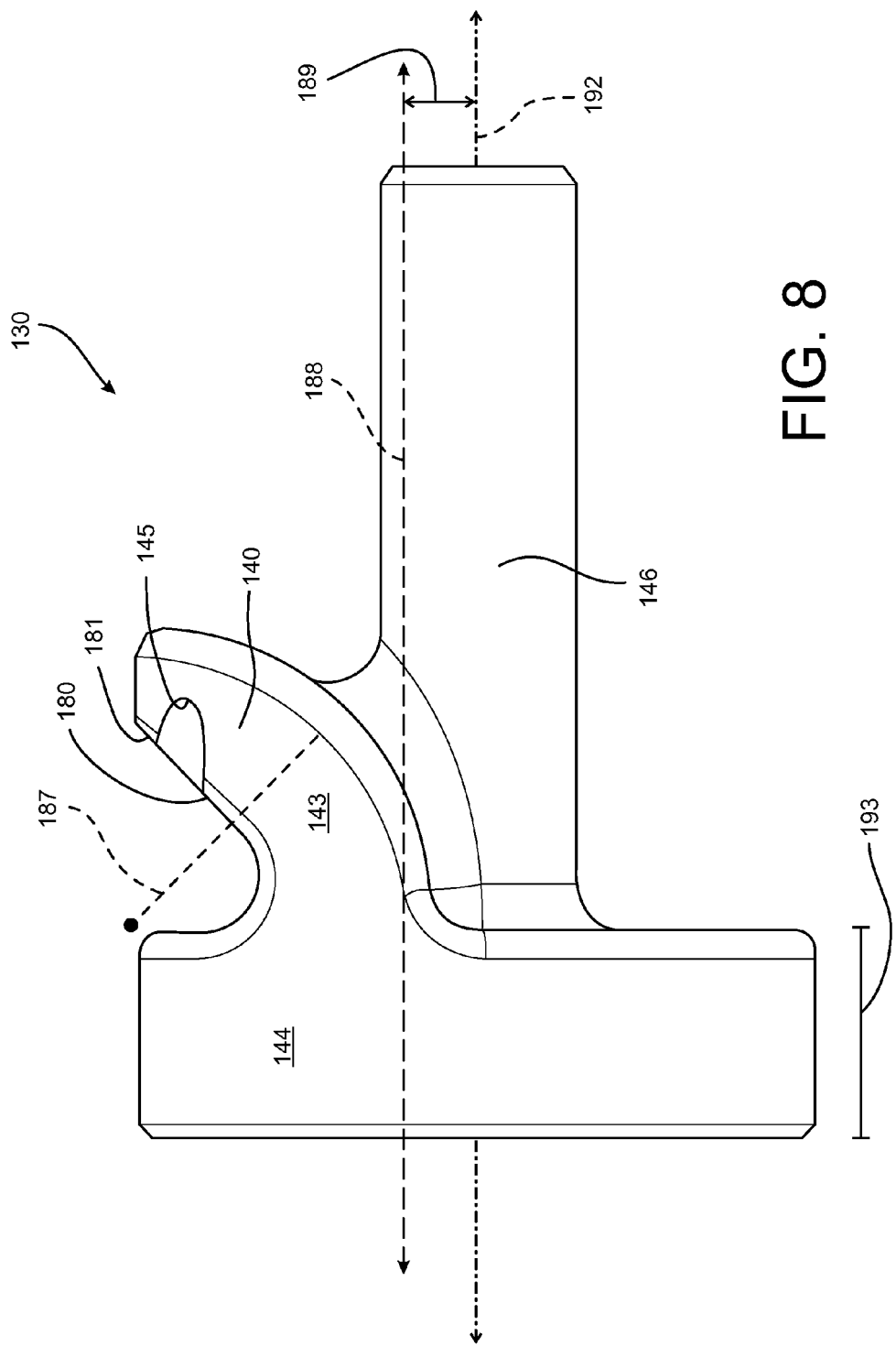
FIG. 8 is a side elevational view of the metaglene component of FIG. 5.

As shown in FIG. 8, the particular size and shape of the metaglene component 130 are dictated by the length of the augment radius 187, the metaglene body thickness 193, and the distance between the medial augment line 188 and the post axis 192, this distance being referred to as the augment displacement 189. Modifications of the particular size and shape of the metaglene component 130 include, for example, lengthening the augment radius 187 without changing the metaglene body thickness 193 or the augment displacement 189. This results in the augment and the metaglene body extending for a longer length relative to the post 146. The size of the void 180 is selected based on the size and shape of the metaglene component 130 such that the void 180 allows for optimized visualization of the lateral augment surface 181 and optimized access to the augment fastener holes 145.

To facilitate selection of the best components for implantation of a prosthetic shoulder, a kit can be formed including components having a variety of shapes and sizes. The kit can include more than one glenoid bearing component 32 having a variety of dimensions. For example, at least one glenoid bearing component 32 can have a larger innermost diameter 65 than another glenoid bearing component 32. The kit can also include more than one metaglene component 30 having a variety of dimensions. For example, at least one metaglene component 30 can have a larger outermost diameter 94 than another metaglene component 30. The kit can also include more than one metaglene component 130 having a variety of dimensions. For example, at least one metaglene component 130 can have a larger augment radius 187 than another metaglene component 130. Additionally, at least one metaglene component 130 can have a larger metaglene body thickness 193 than another metaglene component 130. Additionally, at least one metaglene component 130 can have a larger augment displacement 189 than another metaglene component 130. The kit can also include more than one type of fastener to be used as metaglene body fasteners 156 and as augment fasteners 158.

Using such a kit allows a doctor to select the best combination of components based on a patient's particular bone geometry and defect(s). For example, the doctor could select a glenoid bearing component 32 having a smaller innermost diameter 65 for a patient having a smaller shoulder. The doctor could select a shorter fastener to be used as a metaglene body fastener 156 or augment fastener 158 for a patient having a thinner depth of bone into which the implant is to be fastened. The doctor could also select a metaglene component 130 having the particular combination of larger metaglene body thickness 193, smaller augment displacement 189, and larger augment radius 187 to compensate for a bone defect having a particular depth, width and angle relative to the remaining bone. To further optimize the compensation of the implant and the fixation of the implant into the shoulder bones, the selected metaglene components can be inserted at any degree of rotation and the fasteners can be inserted through the metaglene components and into the bone at a range of angles.

In other embodiments discussed below, the particular size and shape of the metaglene components and voids can be different than those of the embodiment shown in FIGS. 4-8. Each alternative embodiment is suited for a different bone defect in the shoulder and, thus, each has particular benefits.

Figure 9:
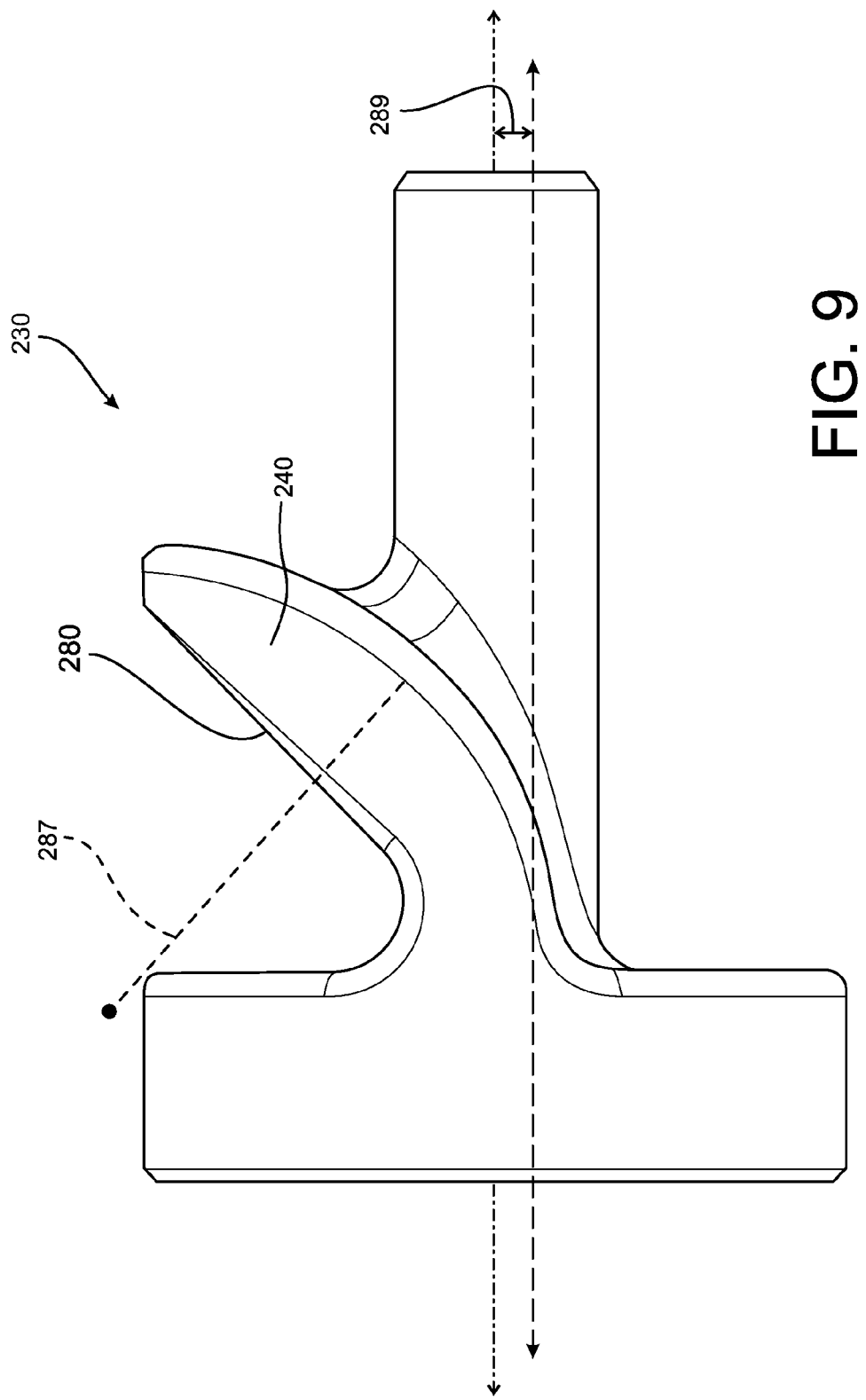
FIG. 9 is an alternative embodiment of a metaglene component configured for use in the metaglene assembly of FIG. 4.

By way of example, FIG. 9 shows an alternative embodiment of a metaglene component 230 that is configured and used in substantially the same manner as the metaglene component 130 described hereinabove. The metaglene component 230 differs from the metaglene component 130, however, in size and configuration of the metaglene component and the void. In particular, the augment displacement 289 is smaller than the augment displacement 189 (shown in FIG. 8). Additionally, the augment displacement 289 is in the opposite direction relative to the void 280 than the augment displacement 189 relative to the void 180 (shown in FIG. 8). The augment radius 287 is larger than the augment radius 187 (shown in FIG. 8). Accordingly, the augment 240 and the void 280 shown in FIG. 9 have different shapes and configurations in relation to the metaglene component 230 than the augment 140 and the void 180 in relation to the metaglene component 130 shown in FIG. 8.

Turning now to FIG. 10, there is shown yet another alternative embodiment of a metaglene component 330 that is configured and used in substantially the same manner as the metaglene component 130 described hereinabove. The metaglene component 330 differs from the metaglene component 130, however, in size and configuration of the metaglene component and the void. In particular, the augment displacement 389 is smaller than the augment displacement 189 (shown in FIG. 8). Additionally, the augment radius 387 is larger than the augment radius 187 (shown in FIG. 8). Accordingly, the augment 340 and the void 380 shown in FIG. 10 have different shapes and configurations in relation to the metaglene component 330 than the augment 140 and the void 180 in relation to the metaglene component 130 shown in FIG. 8.

Although not specifically depicted, additional alternative embodiments can include any combination of augment displacement, augment radius, and metaglene body thickness that results in a functional metaglene component. Additionally, an alternative embodiment can have a combination of an augment displacement and an augment radius such that the post is attached only to the metaglene body or only the augment rather than to both the metaglene body and augment.

There is a plurality of advantages arising from the various features of each of the embodiments of the shoulder prosthesis described herein. It will be noted that alternative embodiments of the shoulder prosthesis may not include all of the features described yet still benefit from at least some of the advantages of such features. Those of ordinary skill in the art may readily devise their own implementations of the shoulder prosthesis that incorporates one or more of the features and fall within the spirit and scope of the present invention as defined by the appended claims.

What is claimed is:

1. A shoulder prosthesis kit, comprising:
    a first metaglene component including (i) a first body defining an outer diameter, (ii) a first augment extending medially from the first body, (iii) a first void defined by a portion of the first body and a portion of the first augment, and (iv) at least one first fastener hole extending from the first void through the first augment;
    a plurality of bearing components, each of the plurality of bearing components defining a cavity configured to couple with the first body, and having a bearing surface that is sized differently from the size of another of the plurality of bearing components; and
    at least one third fastener hole extending from the first void through the first body, wherein:
    a first of the at least one first fastener holes is not aligned with any fastener hole extending through the first body such that a straight fastener cannot extend through the first of the at least one first fastener holes and any fastener hole extending through the first body; and
    a second of the at least one first fastener holes is aligned with a first of the at least one third fastener holes such that a straight fastener can extend through the second of the at least one first fastener holes and the first of the at least one third fastener holes.

2. The shoulder prosthesis kit of claim 1, further comprising:
    a second metaglene component including (i) a second body defining an outer diameter, and (ii) a second augment extending medially from the second body, wherein each of the plurality of bearing component cavities are configured to couple with the second body.

3. The shoulder prosthesis kit of claim 2, wherein the second metaglene component further includes a second void defined by a portion of the second body and a portion of the second augment.

4. The shoulder prosthesis kit of claim 3, wherein:
    the first augment has a size and a shape;
    the second augment has a size and a shape; and
    at least one of the size and the shape of the first augment is different from the size and the shape of the second augment.

5. The shoulder prosthesis kit of claim 3, wherein:
    the first void has a size and a shape;
    the second void has a size and a shape; and
    at least one of the size and the shape of the first void is different from the size and the shape of the second void.

6. The shoulder prosthesis kit of claim 5, wherein:
    the second metaglene component includes at least one second fastener hole extending from the second void through the second augment; and
    the second void and the at least one second fastener hole are is configured such that the at least one fastener can be inserted into the at least one second fastener hole from a medial side of the second body by moving the at least one fastener in a medial direction from the second void into the at least one first fastener hole.

7. The shoulder prosthesis kit of claim 3, wherein:
    the first augment has a first augment radius; and
    the second augment has a second augment radius, the second augment radius being different than the first augment radius.

8. The shoulder prosthesis kit of claim 3, wherein:
    the first metaglene component has a first post axis and a first medial augment line defining a first augment displacement; and
    the second metaglene component has a second post axis and a second medial augment line defining a second augment displacement, the second augment displacement being different than the first augment displacement.

9. The shoulder prosthesis kit of claim 1, wherein the at least one first fastener hole includes a seat defined adjacent to a lateral facing portion of the augment, the seat configured to receive a fastener head of the at least one fastener such that the fastener head does not extend within the void.

10. A metaglene assembly kit for use in a shoulder prosthesis, comprising:
a metaglene component including (i) a metaglene body with a lateral, prosthesis-facing side, and a medial, bone-facing side, (ii) an augment extending medially from the medial, bone-facing side of the metaglene body, (iii) a void defined by a portion of the medial, bone-facing side of the metaglene body and a lateral facing portion of the augment, (iv) a first fastener hole extending from the void through the augment and defining a first fastener hole axis; and (v) a second fastener hole extending through the metaglene body and defining a second fastener hole axis, the second fastener hole axis aligned with the first fastener hole axis such that a straight fastener can extend through the first fastener hole and the second fastener hole; and
a plurality of bearing components, each of the plurality of bearing components defining a cavity configured to couple with the metaglene body, and having a bearing surface that is sized differently from the size of another of the plurality of bearing components.

11. The metaglene assembly kit of claim 10, wherein:
a metaglene body perimeter formed by projecting an end view of the metaglene body onto a plane perpendicular to a longitudinal axis of the metaglene body is approximately circularly shaped;
an augment perimeter formed by projecting an end view of the augment onto the plane is approximately semi-circularly shaped; and
the augment perimeter coincides with at least a portion of the metaglene body perimeter.

12. The metaglene assembly kit of claim 10, further comprising a post extending from at least one of the metaglene body and the augment.

13. The metaglene assembly kit of claim 10, wherein:
the metaglene component further comprises at least one third fastener hole extending from the void through the augment; and
the at least one third fastener hole is not aligned with any fastener hole extending from the void through the metaglene body.

\* \* \* \* \*